(12) United States Patent
Lincoln et al.

(10) Patent No.: US 6,440,971 B1
(45) Date of Patent: Aug. 27, 2002

(54) BINUCLEAR COMPLEX

(75) Inventors: Per Lincoln; Bengt Nordén, both of Göteborg (SE)

(73) Assignee: A+ Science Invest AB, Göteborg (SE)

( * ) Notice: Subject to any disclaimer, the term of this patent is extended or adjusted under 35 U.S.C. 154(b) by 0 days.

(21) Appl. No.: 09/528,173

(22) Filed: Mar. 17, 2000

Related U.S. Application Data (63) Continuation of application No. PCT/SE98/01655, filed on Sep. 16, 1998.

(30) Foreign Application Priority Data

Sep. 19, 1997 (SE) .............................................. 9703396

(51) Int. Cl.$^7$ ...................... A61K 31/50; A61K 31/555; C07F 9/94; C07D 241/46; C07D 515/00
(52) U.S. Cl. ........................ 514/250; 514/185; 514/248; 514/249; 544/225; 544/342; 544/347; 546/48
(58) Field of Search ................................ 514/185, 248, 514/249, 250; 544/225, 347, 342; 546/48

(56) References Cited

FOREIGN PATENT DOCUMENTS

| WO | WO91/03482 | 3/1991 |
|---|---|---|
| WO | WO95/07693 | 3/1995 |

OTHER PUBLICATIONS

P. Pfeiffer et al., "Is Carboplatin and Oral Etoposide an Effective and Feasible Regimen in Patients with Small Cell Lung Cancer?", European Journal of Cancer, vol. 31A, No. 1, pp. 64–69, 1995, Elsevier Science Ltd, Great Britain.

Dae–Kee Kim et al., "Pharmacokinetics and Antitumor Activity of a New Platinum Compound, cis–malonato[(4R, 5R)–4,5–bis(aminomethyl)–2–isopropyl–1,3–dioxolane] platinum(II), as Determined by Ex Vivo Pharmacodynamics", Cancer Chemother Pharmacol, vol. 37, pp. 1–6, 1995, Springer–Verlag, USA.

Francesco Boccardo et al., "Intravesical Idarubicin: A Dose Finding Study", Cancer Chemother Pharmacol, vol. 38, pp. 102–105, 1996, Springer–Verlag, USA.

W. Jonat et al., "A Randomised Study to Compare the Effect of the Luteinising Hormone Releasing Hormone (LHRH) Analogue Goserelin with or without Tamoxifen in Pre–and Perimenopausal Patients with Advanced Breast Cancer", European Journal of Cancer, vol. 31A, No. 2, pp. 137–142, 1995, Elsevier Science Ltd, Great Britain.

Flemming Hansen et al., "Phase II Study of Second–Line Treatment with High–Dose Cyclophosphamide in Recurrent Metastatic Breast Cancer", Cancer Chemother Pharmacol, vol. 37, pp. 377–381, 1996, Springer–Verlag, USA.

J. Vansteenkiste et al., "Combination Chemotherapy with Vindesine–Ifosfamide–Cisplatin (VIP) in Locally Advanced Unresectable Stage III and in Stage IV Non–Small Lung Cancer: A Phase II Trail" Lung Cancer, vol. 13, pp. 295–303, 1995, Elsevier Science Ireland Ltd, Ireland.

"Stereochemically–Defined Supramolecular Architectures: Diastereomerically–Pure Multi–Ru‖Complexes," Dimitrios Tzalis et al., J. Am. Chem. Soc., vol. 119 (1997) pp. 852–853.

"Synthesis, electrochemical and spectroscopic properties of pendant hydroquinone– and quinone–substituted polypyridyl ruthenium(II) complexes," Robert A. Berthon et al., Inorganica Chimica Acta, vol. 204 (1993) pp. 3–7.

Photoinduced energy– and electron–transfer processes in dinuclear ruthenium(II) and/or osmium(II) complexes connected by a linear rigid bis–chelating bridge, Luisa De Cola et al., Recl. Travl. Chim. Pays–Bas, vol. 114 (1995) pp. 534–541.

"The Effect of Some New Platinum (II) and Palladium (II) Coordination Complexes on Rat Hepatic Nuclear Transcription in Vitro," R. Mital et al., Life Sciences, vol. 50 (1992) pp. 781–790.

"Binuclear platinum (II)–terpyridine complexes: A new class of difunctional DNA–intercalating agent," W. David McFadyen et al., Biochem J., vol. 238 ( 1986) pp. 757–763.

"Synthesis, Spectroscopic, Cytotoxic, and DNA Binding Studies of Binuclear 2,2'–Bipyridine–Platinum(II) and—Palladium(II) Complexes of Meso–α, α'–Diaminoadipic and Meso–α, α'–Diaminosuberic Acids," Hassan Mansuri–Torshizi et al., Journal of Inorganic Biochemistry, vol. 45 (1992) pp. 135–148.

"Synthesis, Characterization, DNA Binding, and Cytotoxic Studies of Dinuclear Complexes of Palladium(II) and Platinum(II) with 2,2–Bipyridine and α,ω–Diaminoalkane–N, N'–Diacetic Acid," Nidhi Jain et al., Journal of Inorganic Biochemistry, vol. 53 (1994) pp. 79–94.

Primary Examiner—Mukund J. Shah
Assistant Examiner—Tamthom N. Truong
(74) Attorney, Agent, or Firm—Burns, Doane, Swecker, & Mathis, LLP

(57) ABSTRACT

A binuclear DNA-threading transition metal complex with the general formula: (L1)-M1-(D1-B-D2)-M2-(L2) wherein D1-B-D2 is a bridging ligand; D1 is a polycyclic heteroaromatic ligand in which aza nitrogens can form a bidentate or tridentate chelate with Ml; D2 is any bi- or oligodentate ligand co-ordinated to the transition metal M2; B is any appropriately substituted chain of at least two atoms; M1 is a transition metal ion with octahedral co-ordination sphere; M2 is any transition metal ion; L1 comprises a set of 1–3 ancillary ligands that saturate the remaining co-ordination sphere of M1; and L2 comprises a set of 1–4 ancillary ligands that saturate the remaining co-ordination sphere of M2. An example of the complex according to the invention is shown in the FIG. 1. The complex according to the invention is useful for treatment of different diseases, such as cancer and infections.

24 Claims, 6 Drawing Sheets

*Fig. 1*

Synthesis of (I)

BINUCLEAR COMPLEX

This is a continuation of International Application No PCT/SE98/01655, filed Sep. 16 1998, that designates the United States of America and which claims priority from Swedish Application No. 9703396-3, filed Sep. 19 1997.

FIELD OF THE INVENTION

The present invention relates to binuclear DNA-threading transition metal complex.

BACKGROUND OF THE INVENTION

The use of nucleic-acid binding compounds for pharmaceutical or diagnostic purposes is widespread and goes back many decades in the history of science. Alkylating, strongly binding compounds belonging to this group have for a long time been used for cytostatic treatment. Less strongly binding antibiotics that function by nucleic-acid binding include numerous dyes, some of which are used today as fluorescent markers for DNA, but which originally were developed as drugs against various parasite diseases. Many of these original drugs bind to DNA by intercalating a large planar aromatic entity between two adjacent basepairs of the DNA, whereas some bind into the minor groove of the DNA.

The probably most well-known metal-based drug is the cis-platin compound invented by Rosenberg, which is based on $[cis-Pt(II)Cl_2(NH_3)_2]$. It is believed to interact with DNA in a hydrolysed bis-aquo cationic form, which is intercalated between base-pairs and thereafter to bind to DNA bases by co-ordination to the central metal ion.

Another class of DNA-binding compounds are substitution inert transition metal complexes with an octahedral co-ordination sphere, such as $[Ru(II) (1,10-phenanthroline)_3]^{2+}$, whose DNA adducts are stabilised both by electrostatic attraction to the negative deoxyribophosphate oxygens and by hydrophobic effects due to their lipophilic chelate rings. Due to the octahedral co-ordination, the tris-chelates span all the three spatial dimensions and are inherently chiral, in contrast to the square planar co-ordination complexes of Pt(II) or Pd(II). An interesting possibility, to use the propeller-shaped arrangement of ligands around the central metal to obtain stereochemical recognition of nucleic acid binding sites, has up until the present invention not been very successful, probably because the contact area between complex and nucleic acid is too small.

A DNA-binding drug with two functional groups is in itself not a novel idea. For example, several well known drugs used in cancer therapy consist of one bulky sugar group and one planar polycyclic aromatic group, that is generally believed to be intercalated. Also the "threading" phenomenon, i.e. the fact that a ligand can bind by penetrating through the DNA double helix, having bulky groups in both grooves, is known for several organic-chemical compounds, one example being the antibiotic nogalamycin.

Binuclear metal complexes of Pt(II) and Pd(II) have been described, e.g. in EP-A-0 320 960 and WO 91/03482, but, due to the square planar co-ordination geometry, they lack the stereochemical recognition elements of octahedrally co-ordinated tris-chelates. Also binuclear metal complexes of Pt(IV) which accordingly have an octahedral co-ordination sphere have earlier been described, see e.g. WO 95/07693, WO 88/00947, and WO 84/04524; however, those complexes also lack these stereochemical recognition elements since each Pt(IV) is co-ordinated with at most one substitution-inert bidentate chelating ligand. Platinum based drugs are often associated with problems due to their nephrotoxicity. Non-ionic complexes of Pt(II) have frequently low solubility, and Pt(IV) complexes are likely to be readily reduced to the divalent oxidation state by cell constituents, which in fact may actually be advantageous for activity Without being bound by any mechanism or theory, it is considered likely that chemically inert octahedral complexes with at least one polycyclic heteroaromatic ligand, exemplified by $[Ru(1,10-phenanthroline)_2$ dipyrido$[3,2-a:2',3'-c]$ phenazine$]^{2+}$, act by a completely different mechanism from the platinum based drugs, and that this action is excarted by the intact complex interacting non-covalently with the nucleic acid, i.e. intercalation into DNA (see e.g. Hiort, C. et al, JACS 115 (1993) 348).

SUMMARY OF THE INVENTION

The present invention relates to a binuclear metal complex, in which one of the metals (M1) have octahedral co-ordination and forms substitution-inert co-ordination bonds to the D1 moiety of the bridging ligand and to a second, at least bidentate, ancillary ligand. This gives rise to a chemically stable, chiral as well as sterically demanding and rigid structure at M1, and since D1 is polycyclic, preferably at least tetracyclic, make threading intercalation a likely binding motif to DNA. The link B of the bridging ligand permits enough flexibility that the other metal M2 can approach to and interact with the DNA also when D1 is intercalated.

The binuclear complexes according to the invention comprises stereochemical recognition elements and thus exhibit better recognition properties than the known mononuclear compounds. In addition, a large advantage in comparison with the known compounds is the larger charge and contact area that substantially increases the DNA affinity of these compounds, exploiting both intercalation and groove modes of binding.

Another advantage of the binuclear metal complexes according to the invention is that they have two rigid chiral centra that are connected via a bridge that is rigidly tied to DNA by intercalating groups. The known binuclear Pt or Pd compounds lack these rigid chiral centra.

There are several other advantage of the substitution inert binuclear transition metal complexes according to the invention compared to the known substitution-inert octahedral transition metal complexes, e.g.:

(1) The compounds according to the invention show stronger binding affinity to nucleic acids than known mononuclear compounds,
(2) The compounds according to the invention show a better stereoselection of specific nucleic targets than known mononuclear compounds,
(3) The threading mechanism used by the compounds according to the invention makes both final association and dissociation processes extremely slow. However, an initial fast association leading to a non-threading complex will first occur, which car have unique selection properties. In this way the selection may be controlled not only by thermodynamic features (the final threading geometry) but also by precursory complexes. The applicants call this novel principle of recognition "kinetic recognition".
(4) By filling both of the DNA grooves the binuclear complexes according to the invention will have optimal possibilities to interfere with protein-DNA interaction, for example, for inhibition of transcription or replication. This effect is enhanced due to the very slow dissociation of the threading binuclear complex according to the invention.

(5) By a suitable choice of ligands around the metal centra, the compounds according to the invention can be designed to react covalently with DNA a certain period of time after it has reached its target. In this way recognition properties may be combined with the properties of the covalently reacting tumour drugs.

(6) The slow dissociation and bifunctional nature of the binuclear complexes enhance the efficiency of photochemical reactions with the DNA target, e.g. photocleavage in the case of Rh or Ru complexes.

Furthermore, the high chemical stability of the binuclear complexes exemplified in the invention together with their increased binding affinity and extremely slow dissociation kinetics are likely to make them useful also in cases of Pt-resistant tumours and when the toxicity of platinum agents limits an effective treatment.

BRIEF DESCRIPTION OF THE DRAWINGS

In the description and the claims below reference is be made to the accompanying drawings on which:

DESCRIPTION OF THE INVENTION

The present invention relates to a binuclear transition metal co-ordination complex of a bridging ligand, said complex being constructed in such a way that it can bind to DNA through intercalation of one or both ends of the bridging ligand, thereby placing the middle part of the bridging ligand in one of the grooves of DNA and the transition metal or metals co-ordinated to the intercalating part(s) of the bridging ligand in the opposite groove, i.e. binding by so called threading intercalation, which is a mechanism well known to persons skilled in the art.

The binuclear DNA-threading transition metal complex according to the invention has the general formula wherein:
D1-B-D2 is the above mentioned bridging ligand;
D1, the intercalating part of the bridging ligand, is a polycyclic heteroaromatic ligand, with preferably at least four rings, in which aza nitrogens can form a bidentate or tridentate chelate with M1 and to intercalate with DNA bases;
D2, the other end of the bridging ligand, is identical with or different from D1, and may be any bi- or oligodentate ligand co-ordinated to the transition metal M2;
B, covalently linking the ring system D1 to D2, is any appropriately substituted chain of at least two atoms;

M1 is a transition metal ion with octahedral co-ordination sphere that is capable of forming substitution-inert co-ordination bonds to the D1 moiety of the bridging ligand as well as to at least one of the bi- or polydentate ligands of set L1;
M2 is any transition metal ion;
L1 comprise a set of 1–3 ancillary ligands that saturate the remaining co-ordination sphere of M1; at least one of these ligands forming substitution-inert co-ordination bonds to D1 in a bi-, tri- or tetradentate chelate;
L2 comprises a set of 1–4 ancillary ligands that saturate the remaining co-ordination sphere of M2.

Examples of the ligand D1 are derivatives of dipyrido[3,2-a:2',3'-c]phenazine which co-ordinates to M1 through its pyridine ring nitrogen atoms.

Examples of the ligand D2 are derivatives of dipyrido[3,2-a:2',3'-c]phenazine, in which case the resulting complex of the invention might bis-intercalate into DNA; 1,10-phenanthroline or derivatives thereof; 2,2'-bipyridine or derivatives thereof; 1,2-benzoquinone diimine or derivatives thereof; or 2,2',6',2'-terpyridine or derivatives thereof.

Examples of B are aliphatic, olefinic or aromatic diamines, such as 1,4-diaminobutane, 1,5-diamino-3 -oxapentane, N,N'-diaminopiperazine or 1,4-bis(2-aminoethyl)benzene, forming amide bonds with carboxylic acid derivatives of D1 and D2; aliphatic, olofinic or aromatic dicarboxylic acids, such as glutaric, maileic or terephthalic acids, forming amide bonds with amine derivatives of D1 and D2; or aliphatic, olefinic or aromatic amino acids or peptides connecting D1 and D2 with amide bonds.

Preferred examples of the transition metals M1 and M2 are $Ru^{2+}$, $Os^{2+}$, $Ni^{2+}$ or $Co^{3+}$.

L1 and L2 may e.g. comprise one tetradentate ligand, one tridentate ligand and one monodentate ligand, two bidentate ligands, one bidentate ligand and two monodentate ligands or, in the case of L2, four monodentate ligands. Examples of those ligands are N,N,N-tris(2-aminoethyl)amine (tetradentate); 2,2',6',2"-terpyridine (tridentate); 1,10-phenanthroline, 2,2'-bipyridine (bidentate); imidazol, pyridine (monodentate) or derivatives of these parent ligands. Simple, monodentate ligands may further be water, chloride or ammonia.

The term "derivative" used in the definitions above and elsewhere in this application denotes a ligand compound in which one or more hydrogens of the parent ligand compound, or an aza- , thia- , oxa- or carba-derivative of the parent ligand compound, have been substituted for one or more moieties with the characteristic that the resulting binuclear complex comprising one or more of these ligand derivatives binds to DNA by threading intercalation as described above. Derivatives of 1,10-phenanthroline are e.g. 5,6-dimethyl-1,10-phenanthroline, 4,7-diphenyl-1,10-phenanthroline, 4,7-dichloro-1,10-phenanthroline-3,8-dicarboxamide or pyrazino[2,3-h]-quinoline; derivatives of 2,2'-bipyridine are e.g. 4,4'-dimethyl-2,2'-bipyridine or 2,2'-bipyrazine and derivatives of dipyrido[3,2-a:2',3'-c] phenazine are e.g. dipyrido[3,2-a:2',3'-c]phenazine-11-carboxylic acid, 12-cyano-12,13-dihydro-11H-cyclopentadipyrido[b:3,2-h:2',3'-j]phenazine-12-carboxylic acid or 12-(2-aminoethyl)-11H-imidazo[4,5-b]dipyrido[3,2-h:2',3'-j]phenazine.

The complex according to the invention can be prepared according to several different methods, some of which are exemplified below:
1) Condensation of (L1)-M1-(Q), where (is 1,10-phenanthroline-5,6-dione or a derivative thereof, with (Y-B-D2)-M2-(L2), where Y is an aromatic ortho-diamine chosen so that its condensation with Q gives D1, in an appropriate solvent, such as water, acetonitrile or ethanol, in the presence of a weak acid.

The intermediate (Y-B-D2)-M2-(L2) can be prepared by:

1a) condensation of (L2)-M2-(Q) with an excess of (Y-B-Y'), where Y and Y' are aromatic or heteroaromatic ortho-diamines connected to B as described above. Unless Y=Y' and linker D is symmetric, a mixture of two isomers is obtained. Using instead an excess of (L1)-M1-(Q), symmetrical binuclear complexes, wherein (L1)-M1-(D1)=(L2)-M2-(D2), can be synthesised directly by this route.

The intermediate (Y-B-Y') can be synthesised by:

1a') Reduction of SY-B-SY', where SY and SY' are the 1,2,5-selenadiazole or 1,2,5-thiadiazole derivatives corresponding to Y and Y', respectively, for example by zinc and hydrochloric acid or zinc and acetic acid in ethanol.

The intermediate SY-B-SY' can be synthesised by:

1a") Di-acylation of a diamine by a malonic acid derivative, and subsequent alkylation of the activated methylene groups by an ortho-bis(halomethyl)-substituted 1,2,5-selenadiazol- or 1,2,5-thiadiazol-fused aromatic in the presence of strong base in alcoholic solution.

1b") Use of SY-NH$_2$ or SY'-COX, which may prepared by standard methods from the corresponding ortho-diamines using the procedures described under 3a) and 4a) below.

2) Heating of (L1)-M1-(X)$_2$, where X may be any really displaceable monodentate ligand of M1 such as Cl, H$_2$O or pyridine, with (D1-B-D2)-M2-(L2) in an appropriate solvent, such as aqueous ethanol or ethylene glycol.

The intermediate (D1-B-D2)-M2-(L2) can be synthesised by:

2a) Reaction of (L2)-M2-(X)$_2$ with excess D1-B-D2 as described under 2) above; as the metal may be co-ordinated to D1 as well as to D2 a mixture of isomers is obtained unless D1=D2. Using instead an excess of (L1)-M1-(X)$_2$ binuclear complexes, with (L1)-M1=(L2)-M2 can be synthesised directly by this route;

2b) Condensation of 1,10-phenanthroline-5,6-dione or a derivative thereof with (Y-B-D2)-M2-(L2) as described under 1) above;

2c) Coupling of (D2)-NH$_2$ with (L2)-M -(D2)-E-COX as described under 3) below;

2d) Coupling of (C2)-COX with (L2)-M2-(D2)-E-NH$_2$ as described under 4) below.

3) Coupling of (L1)-M1-(D1)-NH$_2$ with (L 2)-M2-(D2)-E-COX in the presence of a base, such as pyridine or N,N-di(isopropyl)ethylamine in an appropriate solvent, such as dimethylformamide or acetonitrile, wherein E is chosen so that E-CONH-D1=B-D1, and COX is a reactive derivative of a carboxylic acid, such as a chloride, a mixed anhydride or an N-hydroxysuccinimidyl ester.

The intermediate (L2)-M2-(D2)-E-COX can be synthesised by:

3a) Acylation of (L2)-M2-(D2)-NH$_2$ with a derivative of a dicarboxylic acid, such as a cyclic anhydride, e.g. glutaric or succinic anhydride, and subsequent treatment with activating agents, such as oxalyl chloride, dicyclohexyl carbodiimide or N-hydroxysuccinimide-N,N,N',N'-tetramethylisouronium ether; or acylation with an excess of a bifunctional reactive dicarboxylic acid derivative as described under 3) above.

4) Coupling of (L1)-M1-(D1)-COX with (L2)-M2-(D2)-E-NH$_2$ in the presence of a base, such as pyridine or N,N,-di(isopropyl)ethylamine, in an appropriate solvent, such as dimethylformamide or acetonitrile, wherein E is chosen so that E-NHCO-D1=B-D1, and COX is a reactive derivative of a carboxylic acid, such as a chloride, a mixed anhydride or an N-hydroxysuccinimidyl ester.

The intermediate (L2)-M2-(D2)-E-NH$_2$ can be synthesised by:

4a) Reaction of an excess of a diamine, such as 1,6-diaminohexane or spermidine, with (L2)-M2-(D2)-COX as described under 4) above.

The intermediates (L1)-M1-(Q), (L1)-M1-(X)$_2$, (L1)-M1-(D1)-NH$_2$, (L1)-M1-(D1)-COX and D1-B-D2 can be synthesised by standard methods. Unless otherwise specified, the two chiral co-ordination centers of the binuclear complex have a prescribed chirality, denoted by Δ or Λ. This can be achieved by using homochiral intermediates (L1)-M1-(Q) and (L1)-M1-(X)$_2$, for example, the resolution and synthetic use of Ru(1,10-phenanthroline)$_2$-(pyridine)$_2$ and Ru(1,10-phenanthroline)$_2$(1,10-phenanthroline-5,6-dione) have been reported in the literature (see Bosnich, B. & Dwyer, F. P. Aust. J. Chem. 19 (1966) 2229; Hua, X. & von Zelewsky, A. Inorg. Chem. 30 (1991) 3796; Hiort, C. et al. JACS 115 (1993) 3448).

Figure 1:
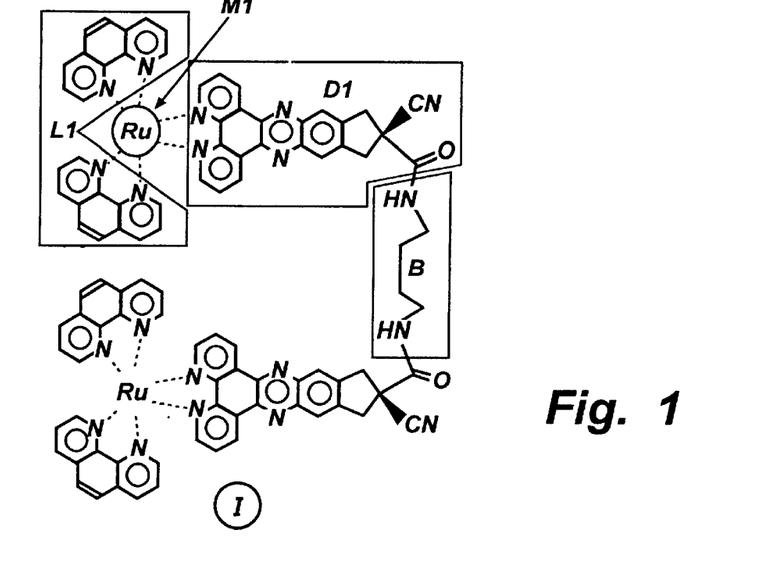
FIG. 1 illustrates an example of the binuclear DNA-threading transition metal complex according to the invention

Several of the binuclear complexes according the invention, including Δ,Δ; Δ,Λ and Λ, Λμ-[N,N'-bis(12-cyano-12,13-dihydro-11H-cyclopentadipyrido[b:3,2-h:2',3'-j]phenazine-12-carbonyl)-1,4-diaminobutane-N$^4$,N$^5$,N$^{'4}$,N$^{'5}$]-tetra (1,10-phenanthroline N$^1$,N$^{10}$) diruthenium(4+) -tetra-chloride, below denominated (I), have been prepared and their DNA binding properties studied. They were found to bis-intercalate into DNA with their D-ligands, which caused a very high affinity for the DNA. Studies of the kinetics of association and dissociation showed these processes to be very slow compared to intercalating mononuclear complexes, which indicate that the bulky L-ligands in fact have to "thread" through the DNA in order to achieve the energetically most stable bis-intercalative binding geometry. The high affinity for DNA and slow dissociation of the resulting addict, is utilised in this invention as a method of killing tumour cells. This is further illustrated in example 7 below. Compound (I) is illustrated in FIG. 1.

The complex according to the invention has several practical applications. It may be used in all situations where one wishes to influence DNA in any way. Examples of those practical applications are, within the pharmaceutical field, drugs and treatment related to cancer as well as drugs and treatment related to infections caused by bacteria, viruses and fungi. The complex according to the invention may be used in order to impose an effect on both the DNA of a patient suffering from a specific disease, as well as the DNA of a microorganism causing the disease.

A further use of the binuclear complexes according to the invention is as photoinduced DNA cleavage agents, either for use with light therapy of tumours or as a laboratory tool, e.g. for diagnostic or analytic purposes.

The present invention will now be further illustrated in the examples below, which in no way are intended to limit the scope of the invention.

EXAMPLES

Example 1

Preparation of N,N'-bis(6-cyano-6,7-dihydro-5-H-1,2,5-selenadiazolo[3,4-f]indene-6-carbonyl)-1,4-diaminobutane (an intermediate of type SY-B-SY') according to the method described under 1a") above 10 mmoles of 1,4-diaminobutane was dissolved in 10 ml methylcyanoacetate and the mixture was refluxed for 30 min under argon. After cooling, the crystalline precipitate of 1,4-bis(cyanoacetamido)butane was filtered off and washed with ether.

1 mmole of 1,4-bis(cyanoacetamido) butane was dissolved in 20 ml of dry methanol together with 6 mmoles of solid sodium methoxide. The solution was heated to boiling, and with vigorous stirring, 3 mmoles of finely ground 5,6-bis(bromomethyl)benzo-1,2,5-selenadiazol (Neidlein, R. & Knecht, D. Ber. 120 (1987) 1593) was added in portions. After a further 30 min of reflux, the mixture was allowed to cool and the precipitated product was filtered off and washed with cold methanol.

Example 2

Preparation of N,N'-bis(5,6-diamino-2-cyano-2,3-dihydro-1H-indene-2-carbonyl)1,4-diaminobutane (an intermediate of type Y-B-Y') according to the method described under 1a') above 30 mmoles of zinc dust was added in portions with stirring to a boiling suspension of 0.5 mmole of N,N'-bis(6-cyano-6,7-dihydro-5-H-1,2,5-selenadiazolo[3,4-f]indene-6-carbonyl)1,4-diaminobutane, Prepared according to example 1, in a mixture of 4 ml concentrated hydrochloric acid and 20 ml ethanol. The mixture was refluxed for a further 20 min, filtered and the filtrate evaporated in vacuo. The syrupy residue was treated with 20 ml of 30% ammonia solution, stirred for 20 min and the product collected by filtration, washed on the filter with aqueous ammonia, water, ethanol and ether. The material was purified by dissolving into a boiling mixture of 20 ml acetonitrile and 10 ml water, filtering and evaporating the acetonitrile with a slow steam of argon until crystals started to form. The mixture was left overnight in a refrigerator, whereafter the crystals were collected by filtration and washed with water, ethanol and ether.

Example 3

Preparation of $\Lambda$-[N-(12-cyano-12,13-dihydro-11H-cyclopentadipyrido[b:3,2-h:2',3'-j]phenazine-12-carbonyl) N'-(5,6-diamino-2-cyano-2,3-dihydro-1H-indene-2-carbonyl)-1,4-diaminobutane $N^4,N^5$]bis(1,10-phenanthroline $N^1,N^{10}$)-ruthenium(2+)-dihexafluorophosphate (an intermediate with formula (Y-B-D2)-M2-(L2)) according to the method described under 1a) above A solution of 0.1 mmoles of $\Lambda$-bis(1,10-phenanthroline $N^1,N^{10}$)(1,10-phenanthroline-5,6-dione $N^1,N^{10}$)-ruthenium (2+)-dihexafluorophosphate (see Hiort, C. et al, JACS 115 (1993) 3448), a compound of type (L1)M1(Q), in 3 ml acetonitrile-water 1:1 was added dropwise with stirring to a hot solution of 0.15 mmoles of N,N'-bis(5,6-diamino-2-cyano-2,3-dihydro-1H-indene-2-carbonyl)1,4-diaminobutane, prepared according to example 2, and 0.5 mmoles of ammonium hexafluorophosphate in a mixture of 5 ml water, 1 ml acetonitrile and 0.5 ml acetic acid. The precipitated orange-red material was collected by filtration and washed with water, ethanol an ether. A small amount of diruthenium complex was removed by chromatography on basic aluminia with acetonitrile as eluent, whereafter the desired product was eluted with 4:1 acetonitrile-ethanol.

Example 4

Preparation of $\Delta,\Lambda$-(I) according to the method described under 1) above 20 $\mu$moles of $\Lambda$-[N-(12-cyano-12,13-dihydro-11H-cyclopentadipyrido[b:3,2-h:2',3'-j]phenazine-12-carbonyl) N'-(5,6-diamino-2-cyano-2,3-dihydro-1H-indene-2-carbonyl)1,4-diaminobutane $N^4,N^5$]bis (1,10-phenanthroline $N^1,N^{10}$)ruthenium(2+)-dihexafluorophosphate, prepared according to example 3, and 40 $\mu$moles of $\Delta$-bis(1,10-phenanthroline $N^1,N^{10}$) (1,10-phenanthroline-5,6-dione $N^1,N^{10}$)ruthenium(2+)-dihexafluorophosphate was dissolved in 0.5 ml acetonitrile containing a drop of acetic acid. After heating on a water bath for 1 h in a closed vial, the product was precipitated by addition of ammonium hexafluorophosphate in ethanol. After filtration and washing with ethanol and ether, the complex was purified by chromatography on basic aluminia with acetonitrile as eluent, and recrystallised from ethanol/acetonitrile.

The product was pure according to TLC ($Al_2O_3$, acetonitrile) and CD (less than 1% of the optical activity of the $\Delta,\Delta$ and $\Lambda,\Lambda$ enantiomers) and characterised by UV-vis and electron-spray MS (mobile phase 60% aqueous acetonitrile; m/e, relative intensities in parenthesis): 440.1 (100%), calc. for $[C_{98}H_{68}N_{20}O_2Ru_2]^{4+}$440.10 635.0 (62%), calc. for $[C_{98}H_{68}N_{20}O_2Ru_2PF_6]^{3+}$635.12; 1024.4 (15%), calc. for $[C_{98}H_{68}N_{20}O_2Ru_2P_2F_{12}]^{2+}$1025.16.

The chloride salt was prepared by precipitation of an acetone solution of the hexafluorophosphate salt with tetrabutylammonium chloride in acetone.

Compound (I) is illustrated in FIG. 1.

Figure 2:
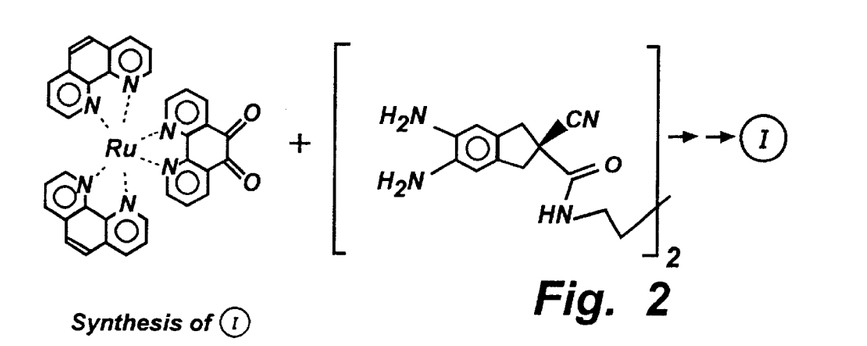
FIG. 2 illustrates a reaction scheme for preparation of the complex according to FIG. 1

A schematic illustration of the reaction scheme is shown in FIG. 2.

Examples 5 and 6

The $\Delta,\Delta$ and $\Lambda,\Lambda$ enantiomers of (I) was prepared analogously to the meso form above in e ample 4 by reacting an excess of the appropriate enantiomer of bis(1,10-phenanthroline $N^1,N^{10}$) (1,10-phenanthroline-5,6-dione $N^1,N_{10}$)ruthenium(2+)-dihexafluorophosphate with the bisortho-diamine, prepared according to example 2.

Example 7

$\Delta,\Delta\mu$-[N,N'-bis(12-cyano-12,13-dihydro-11H-cyclopentadipyrido[b:3,2-h:2',3'-j]phenazine-12-carbonyl)-1,4-diaminobutane $N^4N^5,N^{4'},N^{5'}$]-tetra(2,2'-bipyridine $N^1,N^{1'}$)diruthenium(4+)-tetrachloride, below denominated (II), was prepared by condensation of the bisortho-diamine with an excess of the $\Delta$-enantiomer of the corresponding ruthenium bis-bipyridine phenanthrolinedione complex.

Example 8

By substituting 1,4-diaminobutane in example 1 with ethylenediamine and reducing the selenadiazol as in example 2 N,N'-bis-(5,6-diamino-2-cyano-2,3-dihydro-1H-indene-2-carbonyl)-1,2-diaminoethane is obtained. Condensation of this bis-ortho-diamine with the appropriate phenanthrolinedione complex results in the $\Delta,\Delta$-enantiomers of $\mu$-[N,N'-bis(12-cyano-12,3-dihydro-11H-cyclopentadipyrido[b:3,2-h:2',3'-j]phenazine-12-carbonyl)-1,2-diaminoethane $N^4,N^5,N^{4'},N^{5'}$]-tetra(1,10-phenanthroline $N^1,N^{10}$)-diruthenium(4+)-tetrachloride, below denominated (III) and of $\mu$-[N,N'-bi (12-cyano-12,13-dihydro-11H- cyclopentadipyrido[b:3,2-h:7',3'-j]phenazine-12-carbonyl)-1,2-diaminoethane N$^4$,N$^5$,N$^{4'}$,N$^{5'}$]-tetra(2,2'-bipyridine N$^1$,N$^{1'}$)-diruthenium(4+)-tetrachloride, below denominated (IV).

Example 9

Figure 3A:
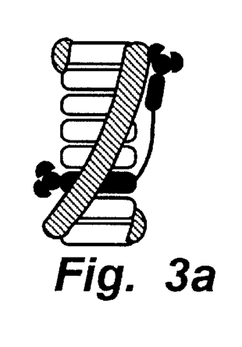
FIG. 3a illustrates a complex according to the invention monointercalated into DNA
Figure 3B:
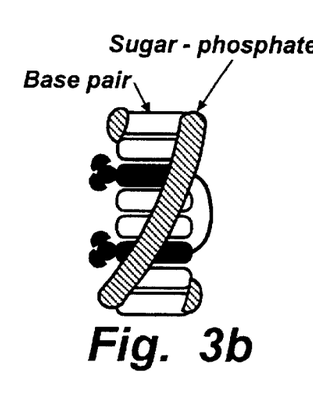
FIG. 3b illustrates a complex according to the invention bisintercalated into DNA
Figure 3C:
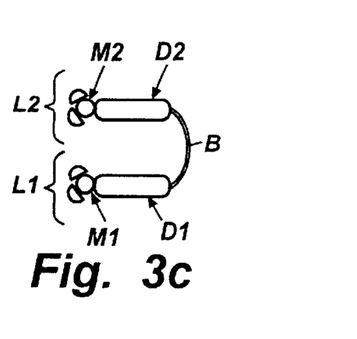
FIG. 3c is a schematic drawing of the complex according to the invention that identifies the different parts of the complexes intercalated according to FIGS. 3a and 3b FIGS. 4a–4e are graphs illustrating the results of the experiments explained below in example 7.

The properties of the Δ,Δ enantiomer of (I) regarding DNA binding was then studied. FIGS. 3a and 3b shows an schematic illustration of proposed modes (I) binding to DNA; FIG. 3a illustrates monointeralation and FIG. 3b illustrates bisintercalation. The results of the studies are shown in FIGS. 4a–e.

Figure 4A:
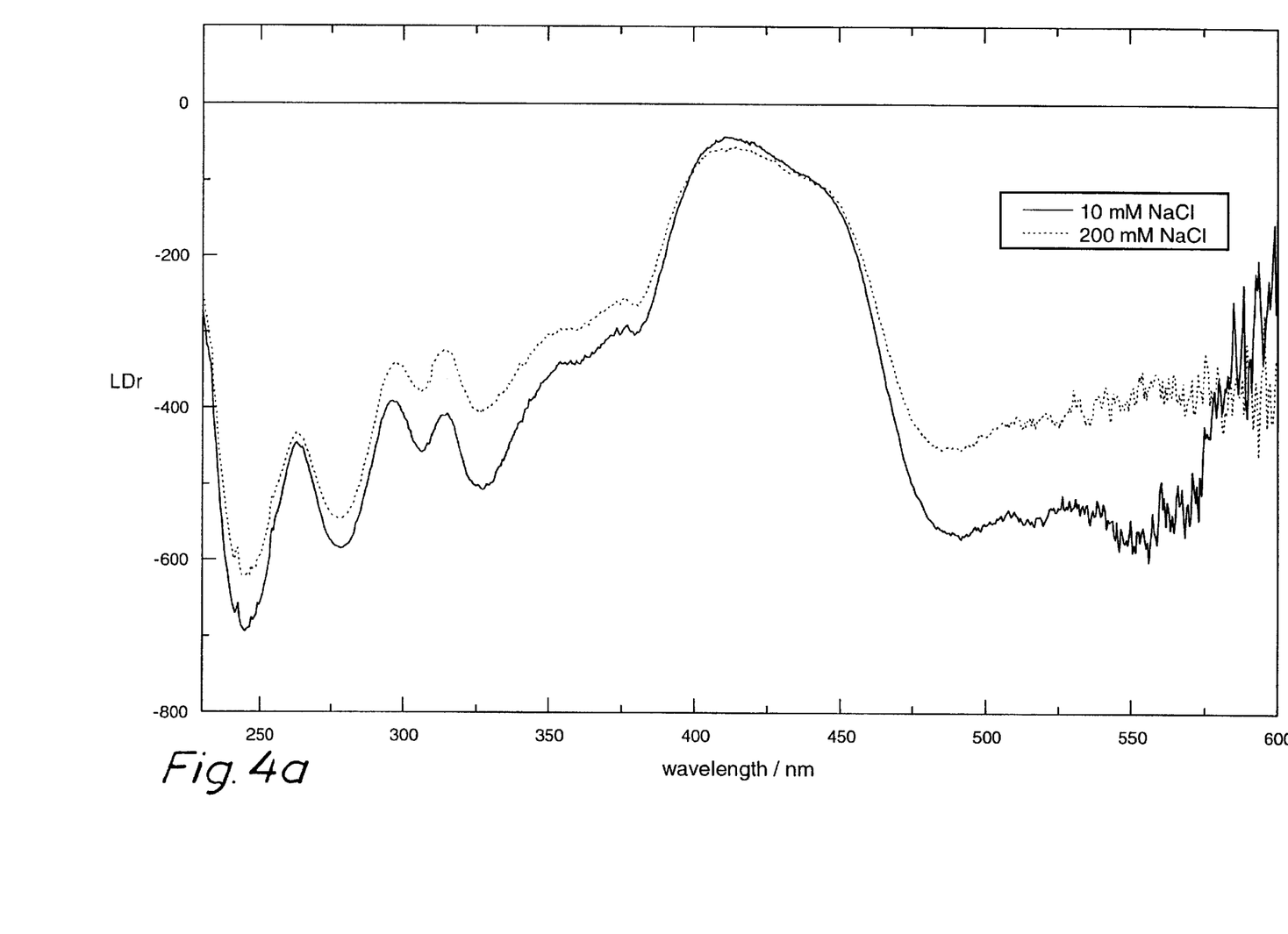

FIG. 4a shows the reduced linear dichroism of the Δ,Δ enantiomer of (I) bound to DNA in 10 mM (solid line) and 200 mM (dotted line) aqueous NaCl solution, [Ru]=5 μM, P/Ru=30. The amplitude of the negative signals 380 and 470 nm indicate bis-intercalation of the complex (Lincoln, P. et al. JACS 118 (1996) 2644).

Figure 4B:
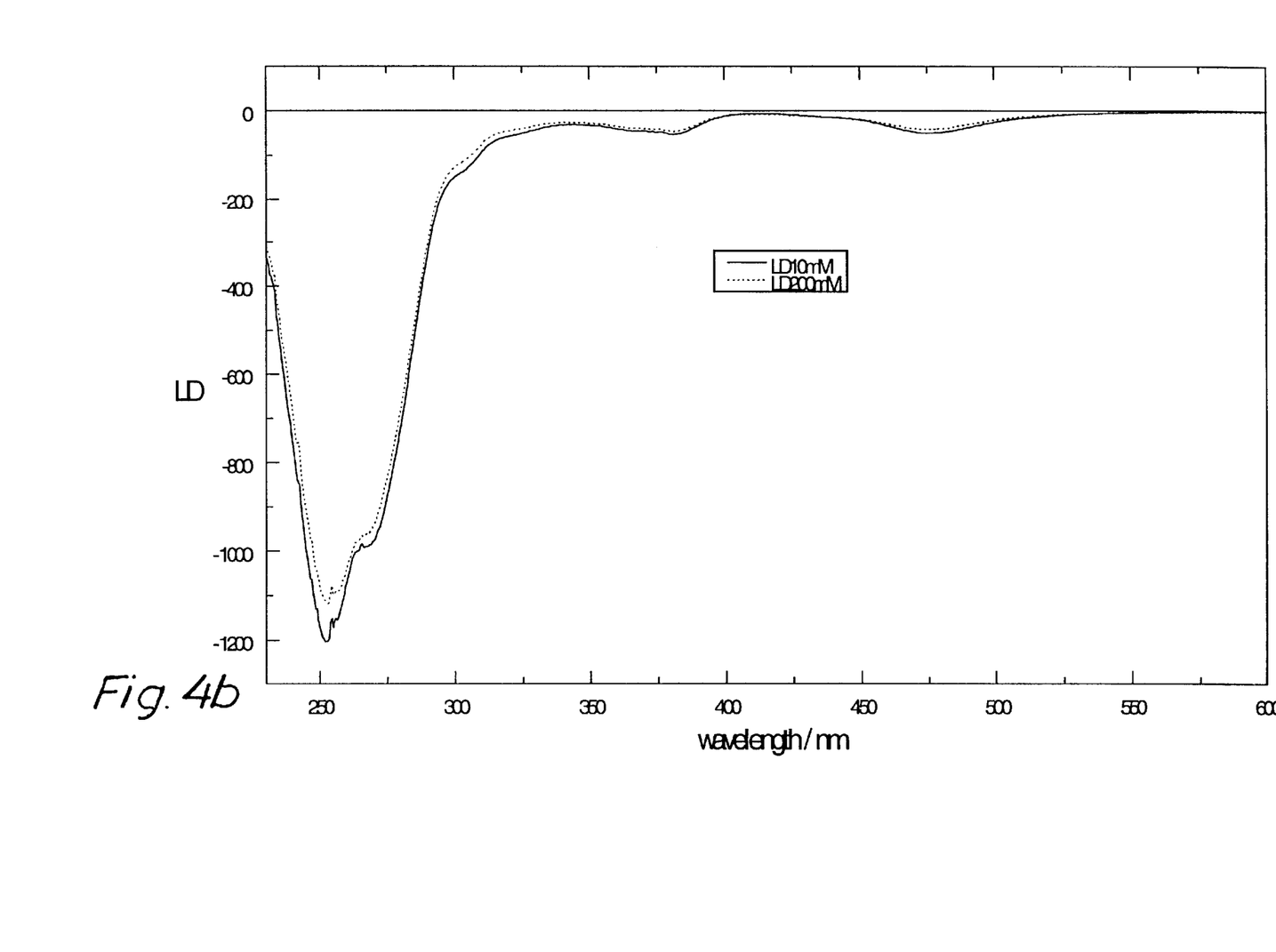

FIG. 4b shows the corresponding linear dichroism spectrum.

Figure 4C:
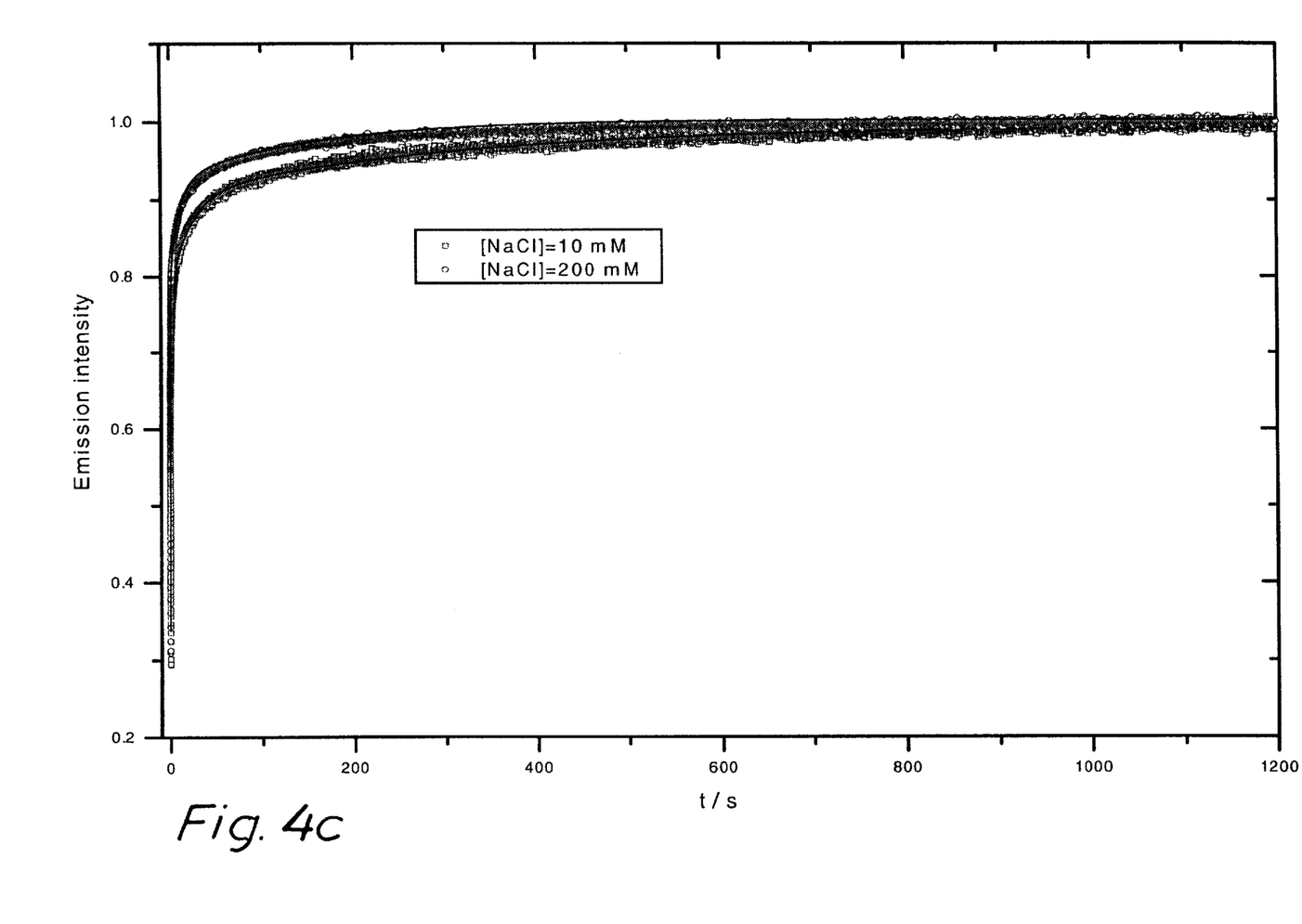
Figure 4D:
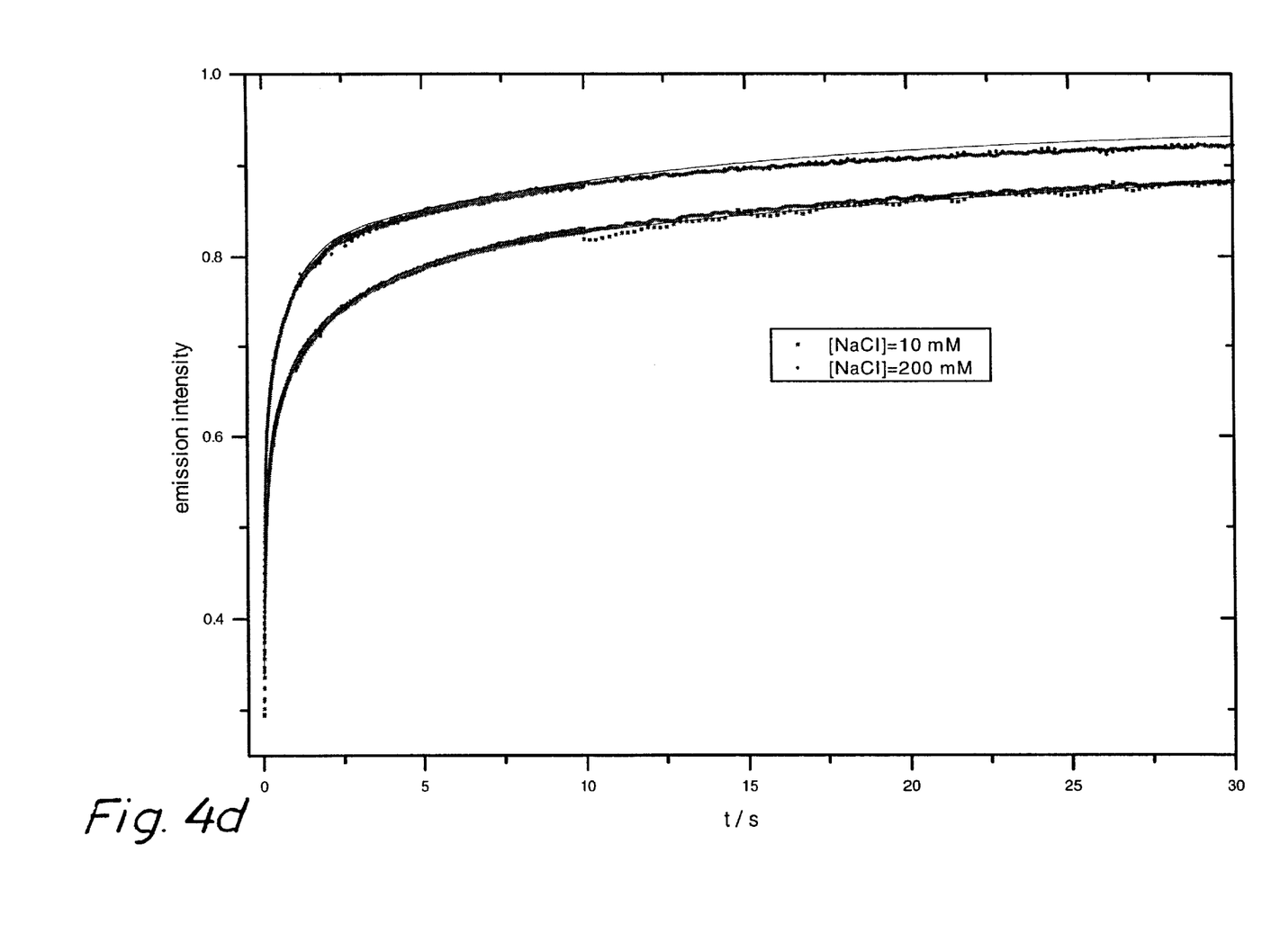

FIG. 4c shows the increase in fluorescence (only bound Ru-complex fluoresces, see Hiort, C. et al, JACS 115 (1993) 3448) with time when Δ,Δ-(I) (2.3 μM Ru) is mixed with calf thymus DNA (P/Ru=67) at 21 C. in the presence of 10 mM (lower curve) and 200 mM (upper curve) NaCl; FIG. 4d is an expansion of the timescale.

Figure 4E:
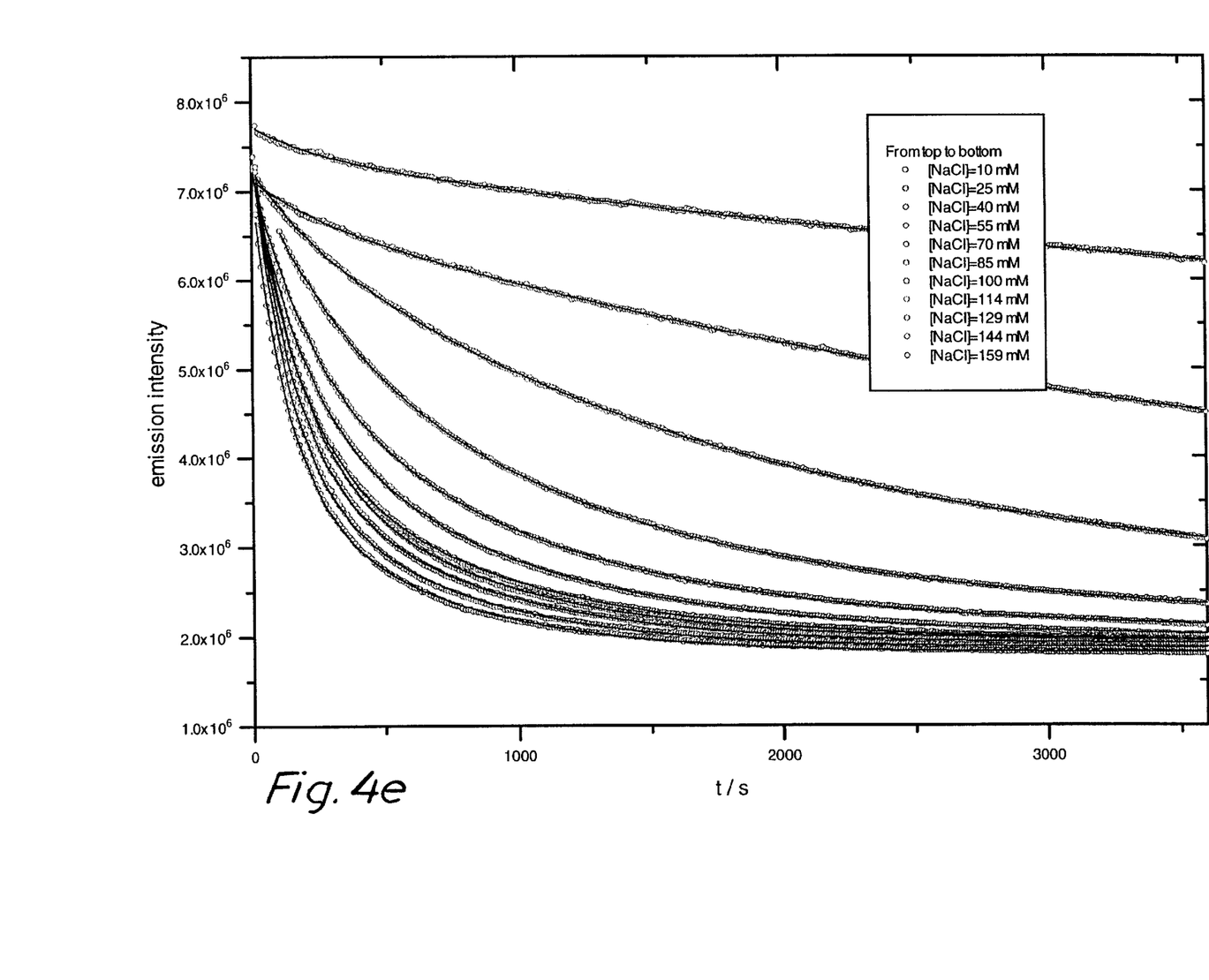

FIG. 4e shows the sodium dodecylsulphate-driven dissociation of the DNA complex at different salt concentrations. While the association reaction is relatively insensitive to the ionic strength of the solution, the dissociation is much faster at physiological salt concentrations, however, the rate constant is still only 0.008 S$^{-1}$ at [NaCl]=159 mM.

Example 10

The growth inhibition of the Δ,Δ-enantiomers of compounds (I), (II), (III) and (IV) according to the invention ware compared to growth inhibit ion of the Δ-enantiomer of the known mononuclear complex [Ru(1,10-phenanthroline)$_2$dipyrido[3,2-a:2',3'-c]phenazine]Cl$_2$, denoted (V) in table 1 below. The result is shown in table 1, which lists the half maximum growth inhibitory concentrations (IC$_{50}$) of the different ruthenium complexes against different tumour cell lines. The IC$_{50}$ values are given in μmoles per liter. It is clearly evident that the binuclear complexes according to the invention have higher activity than the known mononuclear complex.

TABLE 1

| Tumour cell line: | Compound: | | | | |
| --- | --- | --- | --- | --- | --- |
|  | (I) | (II) | (III) | (IV) | (V) |
| Lung carcinoma HBT182 | 9 | 8 | 19 | 10 | 38 |
| Melanoma | 19 | 30 | 19 | 45 | >50* |
| SUDHL 1 | 14 | 12 | 14 | 22 | 39 |
| LAMA | 8 | 9 | 12 | 16 | 43 |

*17% growth inhibition at 50 mM

What is claimed:

1. A binuclear DNA-threading transition metal complex with the general formula (L1)-M1-(D1-B-D2)-M2-(L2)

wherein:
   D1-B-D2 is a bridging ligand;
   D1 and/or D2 are a substituent having an optionally substituted cyclopentadipyrido[b:3,2-h: 2',3'-j]phenazine-12-carboxylic acid;
   B, covalently linking the ring system D1 to D2, is any appropriately substituted chain of at least two atoms;
   M1 is a transition metal ion with octahedral co-ordination sphere that is capable of forming substitution-inert co-ordination bonds to the D1 moiety of the bridging ligand as well as to at least one of the bi- or polydentate ligands of set L1;
   M2 is any transition metal ion; and
   L1 and/or L2 are a substituent having pyridyl groups, said pyridyl groups selected from the group consisting of 2,2'-bipyridine, 4,4'-dimethyl-2,2'-bipyridine and 2,2',6'2"-terpyridine.

2. A complex according to claim 1, wherein the linking chain B is derive from a diamine, a dicarboxylic acid, an amino acid or a peptide.

3. A complex according to claim 2, wherein B is 1,4-diaminobutane, 1,5-diamino-3-oxapentane, N,N'-diaminopiperazine or 1,4-bis(2-aminoethyl)benzene; glutaric, maleic or terephthalic acid; 1,2-diaminoethane, 1,3-diaminopropane, 1,4-diaminobutane, 1,5-diaminopentane or 1,6-diaminohexane.

4. A complex according to claim 1, wherein L1 and L2 comprise at least one of the following ligands: 2,2',6',2"-terpyridine; 2,2'-bipyridine; imidazol, pyridine or derivatives thereof; water, chloride or ammonia.

5. A complex according to claim 1, wherein L1 and L2=(R)$_2$, R being a compound selected from the group consisting of 2,2-bipyridine, and 4,4'-dimethyl-2,2'-bipyridine and 2,2'-bipyrazine or derivatives thereof.

6. A complex according to claim 1, wherein D1 and D2 are 12-cyano-12,13-dihydro-11H-cyclopentadipyrido[b:3,2-h:2'3-j]phenazine-12-carboxylic acid.

7. A complex according to claim 1, wherein M1 and M2 is Ru, Co, Os, Fe, Rh or Ni.

8. A cytostatic composition comprising a cytostatically effective amount of a complex according to claim 1.

9. An antibiotic comprising an anti-microbially effective amount of a complex according to claim 1.

10. A method of treating cancer by administration of an effective amount of a complex according to claim 1.

11. A method of treating infection by administration of an effective amount of a complex according to claim 1.

12. A method of producing a composition suitable for treatment of cancer and tumors comprising an anti-tumor effective amount of a complex according to claim 1 with a pharmaceutically acceptable carrier.

13. A method of producing a composition suitable for treatment of infections comprising combining an amount of a complex according to claim 1 effective to treat infection with a pharmaceutically acceptable carrier.

14. A method of producing a composition suitable for inducing photocleavage of a nucleic acid sequence comprising combining an amount of a complex according to claim 1 effective to induce nucleic acid cleavage upon in vivo administration to a host, and a pharmaceutically acceptable carrier.

15. A pharmaceutical composition comprising a binuclear DNA-threading transition metal complex with the general formula (L1)-M1-(D1-B-D2)-M2-(L2)

wherein:
   D1-B-D2 is a bridging ligand;
   D1 and/or D2 are a substituent having an optionally substituted cyclopentadipyrido[b:3,2-h: 2',3'-j]phenazine-12-carboxylic acid;

B, covalently linking the ring system D1 to D2, is any appropriately substituted chain of at least two atoms;

M1 is a transition metal ion with octahedral co-ordination sphere that is capable of forming substitution-inert co-ordination bonds to the D1 moiety of the bridging ligand as well as to at least one of the bi- or polydentate ligands of set L1;

M2 is any transition metal ion; and

L1 and/or L2 are a substituent having pyridyl groups, said pyridyl group selected from the group consisting of 2,2'-bipyridine, 4,4'-dimethyl-2,2'-bipyridine and 2,2',6'2"-terpyridine.

16. A pharmaceutical composition according to claim 15, wherein the linking chain B is derived from a diamine, a dicarboxylic acid, an amino acid or a peptide.

17. A pharmaceutical composition according to claim 16, wherein B is 1,4-diaminobutane, 1,5-diamino-3-oxapentane, N,N'-diaminopiperazine or 1,4-bis(2-aminoethyl)benzene; glutaric, maleic or terephthalic acid; 1,2-diaminoethane, 1,3-diaminopropane, 1,4-diaminobutane, 1,5-diaminopentane or 1,6-diaminohexane.

18. A pharmaceutical composition according to claim 15, wherein L1 and L2 comprise at least one of the following ligands: 2,2',6',2"-terpyridine; 2,2'-bipyridine; pyridine or derivatives thereof; water, chloride or ammonia.

19. A pharmaceutical composition according to claim 15, wherein L1 and L2=$(R)_2$, R being a compound selected from the group consisting of 2,2'-bipyridine, and 4,4'-dimethyl-2,2'-bipyridine and 2,2'-bipyrazine or derivatives thereof.

20. A pharmaceutical composition according to claim 15, wherein D1 and D2 are 12-cyano-12,13-dihydro-11H-cyclopentadipyrido[b:3,2-h:2'3'-j]phenazine-12-carboxylic acid.

21. A pharmaceutical composition according to claim 15, wherein D1 and M2 is Ru, Co, Os, Fe, Rh or Ni.

22. A pharmaceutical composition according to claim 15, which is suitable for treatment of cancer and tumors in a subject in need of such treatment.

23. A pharmaceutical composition according to claim 15, which is suitable for treatment of an infection in a subject in need of such treatment.

24. A method of treating infection by administration of an effective amount of a pharmaceutical composition according to claim 15.

* * * * *